United States Patent [19]
Kurtz et al.

[11] 3,987,119
[45] Oct. 19, 1976

[54] PRODUCTION OF VINYL CHLORIDE FROM ETHANE

[75] Inventors: Bruce E. Kurtz, Marcellus; Edmund W. Smalley, Brewerton, both of N.Y.; Walter E. Sommerman, Mountain Lakes, N.J.; John R. Van Atta, De Witt, N.Y.

[73] Assignee: Allied Chemical Corporation, Morris Township, N.J.

[22] Filed: Oct. 23, 1973

[21] Appl. No.: 408,956

[52] U.S. Cl. .................. 260/656 R; 260/659 A; 260/683.3
[51] Int. Cl.² ........................................ C07C 21/02
[58] Field of Search.......... 260/656 R, 654 A, 683.3

[56] References Cited
UNITED STATES PATENTS

| | | | |
|---|---|---|---|
| 3,055,955 | 9/1962 | Hodges | 260/656 |
| 3,308,197 | 3/1967 | Bajars | 260/656 |
| 3,336,412 | 8/1967 | Lyon | 260/679 |
| 3,658,933 | 4/1972 | Beard | 260/683.3 |
| 3,658,934 | 4/1972 | Beard | 260/683.3 |
| 3,702,311 | 11/1972 | Beard | 260/683.3 |
| 3,862,996 | 1/1975 | Beard | 260/677 |

FOREIGN PATENTS OR APPLICATIONS

| | | | |
|---|---|---|---|
| 926,783 | 5/1963 | United Kingdom | 260/656 |

Primary Examiner—James O. Thomas, Jr.
Assistant Examiner—A. Siegel
Attorney, Agent, or Firm—Gerard P. Rooney; Gerhard H. Fuchs; Jack B. Murray, Jr.

[57] ABSTRACT

A process is disclosed for the production of ethylene dichloride from ethane. Ethane is introduced into an autothermic (self-sustaining) cracking zone together with controlled proportions of chlorine and oxygen. The autothermic cracking zone is maintained at a temperature above about 700° C. but below 1000° C. for a sufficient time to convert from about 20 to 95 percent of the ethane having about 96 to 74 percent ethylene yield, respectively, based on the converted ethane. The reaction mixture, containing predominantly ethylene and hydrogen chloride, is quenched with a volatile liquid. The quenched mixture is passed, together with oxygen, into a catalytically activated oxyhydrochlorination zone to convert the ethylene, hydrogen chloride and oxygen to ethylene dichloride. If vinyl chloride is desired as a product, part or all of the produced ethylene dichloride is passed to a second cracking zone for conversion to vinyl chloride product and hydrogen chloride. The hydrogen chloride produced is recycled to the oxyhydrochlorination zone. Ethylene dichloride, vinyl chloride or mixtures of ethylene dichloride and vinyl chloride can be recovered as product, with substantially complete utilization of the hydrogen chloride produced.

5 Claims, 1 Drawing Figure

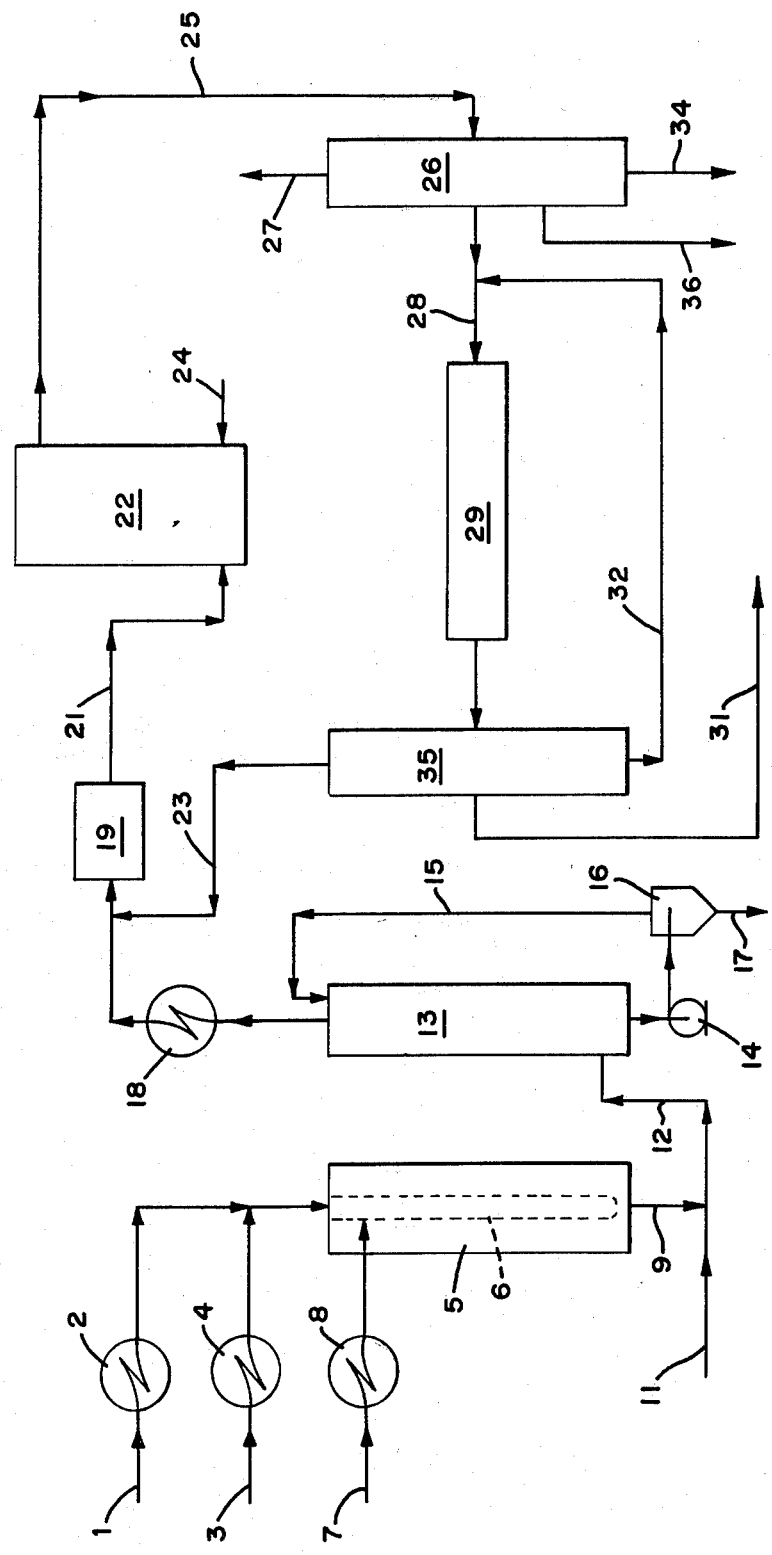

3,987,119

PRODUCTION OF VINYL CHLORIDE FROM ETHANE

BACKGROUND OF THE INVENTION

1. Field of the Invention

The technology for producing ethylene dichloride and vinyl chloride has undergone major changes in the past decade. Until the mid-1960's vinyl chloride was generally manufactured by the hydrochlorination of acetylene. Acetylene, however, is substantially more costly than ethylene; hence, strong motivation existed to develop a process based entirely on ethylene. Such a process was successfully developed in the past, having as its key step, the oxyhydrochlorination of ethylene to ethylene dichloride. As a result, the acetylene-based process has, in recent years, been almost completely replaced by the more economical ethylene-based process.

2. Description of the Prior Art

While ethane is even less expensive than ethylene and consequently considerable effort has been expended in the past to develop an ethane-based ethylene dichloride process, these efforts, however, did not culminate in a commercially adaptable process.

SUMMARY OF THE INVENTION

It has been found that when ethane is subjected to autothermic cracking in the presence of specified amounts of chlorine and oxygen, and under specified conditions of time and temperature, high conversions of ethane ranging from 20 to 98 percent with concomitant production of ethylene in yields based on the converted ethane ranging from 100 to 70 percent can be obtained without the need for catalytic agents. The term "oxygen" herein means oxygen gas or an oxygen-containing gas such as air. Cracking which does not require the continuous input of large quantities of heat is referred to herein as "autothermic" cracking. Autothermic cracking minimizes heat input requirements, capital investment requirements, recycling, and by-product and carbon formation. This autothermic cracking operation comprises a step in a process for economic production of ethylene dichloride in high yield. The cracking step can be controlled so that only hydrogen chloride actually required in the production of ethylene dichloride is formed. The raw materials are ethane, chlorine and oxygen. The oxygen can, if desired, be entirely supplied by air.

The autothermic cracking process of our invention for use in the production of ethylene from ethane is as follows: Ethane, chlorine and oxygen are introduced, preferably after preheating, as reactants into an autothermic reaction zone in controlled proportions, with a molar ratio of chlorine:ethane of from about 0.2 to 1.2:1 and a molar ratio of oxygen:ethane of from about 0.005 to 0.5:1, preferably between about 0.1:1 and 0.4:1. The reactants are maintained in the reaction zone under autothermic cracking conditions including a temperature ranging from above about 700° C. to below 1000° C., preferably between about 850° C. to 950° C., for a time period of from about 0.1 to 10 seconds, preferably between about 0.25 and 2.5 seconds. Products of this autothermic reaction comprise a major amount of ethylene and hydrogen chloride and a minor amount of water, methane, carbon monoxide, hydrogen and acetylene. Thereafter this reaction product stream is cooled, preferably by quenching with a volatile liquid such as water and preferably to a reaction product temperature below about 600° C. Then the quenched autothermic reaction products may be further reacted to obtain, as desired final product, ethylene dichloride, vinyl chloride, or a mixture of ethylene dichloride and vinyl chloride.

Where ethylene dichloride is desired as final product, the quenched autothermic reaction product containing ethylene and hydrogen chloride is passed together with oxygen to a catalytically activated oxyhydrochlorination zone under oxychlorination conditions sufficient to convert the ethylene, hydrogen chloride and oxygen to ethylene dichloride. Thereafter the ethylene dichloride is recovered as product. When ethylene dichloride is the desired product, the preferable molar ratio of chlorine:ethane in the autothermic cracking reaction zone is maintained between about 0.9:1 and 1.2:1.

Where vinyl chloride is desired as final product, all of the ethylene dichloride produced in the oxyhydrochlorination zone is passed to an externally heated cracking zone so as to convert ethylene dichloride to vinyl chloride and hydrogen chloride. The vinyl chloride is recovered as product. Thereafter the hydrogen chloride formed in the externally heated cracking zone is recycled to the oxyhydrochlorination zone. Preferably the ethylene dichloride which is not converted to vinyl chloride in the externally heated cracking zone is recycled to the externally heated cracking zone. When vinyl chloride is the desired product, the preferable molar ratio of chlorine:ethane in the autothermic cracking reaction zone is maintained between about 0.4:1 and 0.6:1.

Where both vinyl chloride and ethylene dichloride are desired as final products, a portion of the ethylene dichloride produced in the oxyhydrochlorination zone is removed therefrom and recovered as a product. The remaining amount of the ethylene dichloride produced in the oxyhydrochlorination zone is passed to an externally heated cracking zone under conditions sufficient to convert ethylene dichloride to vinyl chloride and hydrogen chloride. The vinyl chloride is recovered as product. The hydrogen chloride formed in the externally heated cracking zone is recycled to the oxyhydrochlorination zone. Preferably, chlorine introduced into the autothermic reaction zone is increased beyond that required for vinyl chloride as product by the chlorine equivalent to the portion of the ethylene dichloride which is removed as product. When both vinyl chloride and ethylene dichloride are the desired products, the preferable molar ratio of chlorine:ethane in the autothermic cracking reaction zone is maintained between about 0.6:1 and 0.9:1.

BRIEF DESCRIPTION OF THE DRAWING

The accompanying diagram illustrates the manner in which ethane may be converted in good yield in a single pass to ethylene in accordance with a preferred embodiment of our invention. The ethylene may be used in the production of ethylene dichloride, mixtures of vinyl chloride and ethylene dichloride, or vinyl chloride. The autothermic cracking of ethane in the presence of controlled amounts of chlorine and oxygen, and within the preferred temperature range of our process, produces ethylene in high yield, as well as hydrogen chloride. Both the ethylene and the hydrogen chloride are consumed in the production of ethylene dichloride. The flow diagram also illustrates one way in which the ethylene and hydrogen chloride produced in the autothermic cracking step can be utilized in the economic production of vinyl chloride as the final product.

With reference to the drawing, chlorine in line 1 is preheated in heat exchanger 2, and mixed with oxygen entering at line 3, which is preheated in heat exchanger 4. The molar ratio of chlorine to ethane is from 0.2 to 1.2:1, and the molar ratio of oxygen to ethane is from 0.005 to 0.5:1. The hot gaseous mixture is introduced into reaction chamber 6 of gas-gas reactor 5. Ethane gas in line 7 is preheated in heat exchanger 8, and enters reactor chamber 6 simultaneously with the stream of chlorine and oxygen. Autothermic cracking takes place at a temperature from about 700° C. to below 1000° C. for a retention time from about 0.1 to 10 seconds. Autothermic cracking can be controlled by varying the composition of the feed, the degree of preheating, the reaction temperature and the retention time to obtain conversion of between about 20 and 98 percent of the ethane, with yields of ethylene, based on the converted ethane, of from about 100 to 70%. The hot reaction product comprising predominantly ethylene and hydrogen chloride leaves the reactor at line 9 and is cooled, preferably quenched by a volatile liquid which is substantially unreactive toward the reaction products and which enters at line 11. The quenched mixture, which also contains by-products and carbon, passes through line 12 to scrubber 13 through which quench liquid circulates via line 15, by means of pump 14. A solids separator is shown at 16 for collection and removal of particulate carbon at line 17.

Ethylene, hydrogen chloride and by-products including acetylene are reheated at heat exchanger 18 to at least about 150° C. to 200° C. and passed through a catalytically activated hydrogenator 19 containing a conventional hydrogenation catalyst such as palladium or activated alumina, which converts the acetylene present to ethylene.

Ethylene and hydrogen chloride leaving the hydrogenator 19 pass through line 21 to the oxyhydrochlorinator 22. This may be a conventional fixed or fluid bed oxyhydrochlorinator having a conventional catalyst such as copper chloride on an alumina base. The oxyhydrochlorinator operates within a temperature range of about 200° C. to 250° C. Additional hydrogen chloride from the subsequent cracking of ethylene dichloride is also received through line 23. Oxygen (or air) enters oxyhydrochlorinator 22 through line 24. The ethylene dichloride produced, together with by-products, passes through line 25 to recovery system 26. Non-condensibles are separated via line 27, among them being unreacted ethane. If substantially pure oxygen gas is used, rather than air, this ethane which is generally contaminated with carbon monoxide, hydrogen and methane may, after removal of carbon monoxide and purging of methane, be recycled through line 7 and heat exchanger 8 to the autothermic cracking reactor 5. The concentration of the contaminating methane is held to a low value, preferably by employing a continuous purge, while the carbon monoxide is removed by conventional means, such as by scrubbing with acidic cuprous chloride solution. Water is removed from the recovery system 26 at line 34.

If vinyl chloride is to be a final product, the separated ethylene dichloride leaves recovery system 26 through line 28, and is thermally cracked by passage through tublar furnace 29 at a temperature such that products exit at about 500° C. to 600° C. producing vinyl chloride. The vinyl chloride is withdrawn from recovery system 35 for further purification or storage via line 31. If, on the other hand, ethylene dichloride is to be the product, or if it is to be recovered together with vinyl chloride, it is withdrawn through line 36. When part or all of the ethylene dichloride leaving recovery system 26 is to be thermally cracked to produce vinyl chloride and hydrogen chloride at thermal cracking unit 29, the hydrogen chloride is recovered in recovery system 35 and passed through line 23 to join the ethylene and hydrogen chloride stream enroute to the oxyhydrochlorinator 22 via line 21. Unconverted ethylene dichloride is recycled from recovery system 35 to the tubular cracking furnace 29 through line 32.

DESCRIPTION OF THE PREFERRED EMBODIMENT

The ethane-based ethylene dichloride process of the present invention involves two main reactions: the autothermic cracking of ethane; and the oxhydrochlorination of ethylene. If vinyl chloride is desired as product, it is produced by thermal cracking of ethylene dichloride. The combination of these three reactions constitutes an overall process for vinyl chloride production.

1. Autothermic Cracking of Ethane to Ethylene

The key reaction step is the autothermic cracking of ethane.

Maximization of the ethylene yield is largely a matter of proper reactant ratios, temperature and residence time.

All the reactants may be preheated before passage into the autothermic cracking zone but it is preferable to avoid temperatures above 600° C. for ethane so as to prevent thermal cracking and to avoid temperatures above 400° C. for chlorine so as to protect the processing equipment. At elevated temperatures chlorine becomes highly corrosive.

The degree of preheating of reactants and the proportions of reactants used in the autothermic reaction zone will affect reaction temperature, reaction efficiency and protect purity. Increasing the oxygen input will raise the temperature; but as the ratio of oxygen to ethane is increased, the quantity of by-products, particularly carbon monoxide and methane, is also increased with a corresponding decrease in ethylene yield. Also, small amounts of free hydrogen are formed during the autothermic reaction. Such free hydrogen formation makes it possible to use less than the "theoretical" oxygen-to-ethane molar ratio, thus reducing the formation of carbon monoxide. However, free hydrogen also tends to reduce the heat of reaction of the autothermic cracking step and thus to increase the temperature to which the reactants must be pre-heated. In general, the theoretical oxygen-to-ethane ($O_2/C_2H_6$) molar ratio can be defined as $(1-x)/2$ where $x = Cl_2/C_2H_6$, i.e.

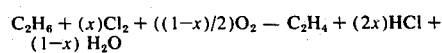

Hence, a "theoretical" oxygen/ethane molar ratio of 0.25 applies if the chlorine/ethane molar ratio is 0.50:

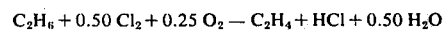

The actual temperatures chosen for preheating the chlorine, as well as the air and ethane, should be those found best to achieve a temperature ranging from above about 700° C. to below 1000° C., preferably between about 850° C. and 950° C., in the autothermic cracking unit.

The heat exchangers for preheating feed gases to the autothermic reactor can be included in a single unit, comprising for example, coils or tube bundles in a single encompassing heater. Also, if desired, such coils or tube bundles can be included in an encompassing "hot box" or "heated zone" which includes the autothermic reaction zone of a multiplicity of tubular reactors arranged for parallel operation.

The reactants are maintained in the reaction zone for at least about 0.1 second, preferably between about 0.25 to 2.5 seconds, or for a time sufficient to convert concomitantly from about 20 to 98 percent of the ethane to 100 to 70 percent of the ethylene, respectively, based on the converted ethane. The autothermic cracking products stream comprises mainly ethylene and hydrogen chloride, with smaller amounts of water, methane, carbon monoxide, hydrogen and acetylene.

The conversion and yields obtained are much better at temperatures ranging from above about 700° C. to below 1000° C. and retention times of from about 0.1 to 10 seconds than when the autothermic cracking step is carried out at temperatures in excess of 1000° C. with retention times of less than 0.1 second. The percent conversion of ethane and the percent ethylene yield, based on the ethane converted, bear approximately an inverse relationship as shown in the tabulation below. The results shown were determined at a chlorine:ethane ratio of about 0.5:1 and an oxygen:ethane ratio of about 0.1:1.

| Conversion | Yield |
|---|---|
| 20% | 96% |
| 40% | 95% |
| 60% | 93% |
| 80% | 87% |
| 90% | 80% |
| 95% | 74% |

By lowering the reactor temperature or decreasing residence time, the conversion is decreased and the yield increased. At an ethane conversion of about 70%, the ethylene yield is about 90% and the ethylene yield per pass (conversion times yield) is 63%. Increasing conversion decreases yield so that at a conversion of 95%, the yield of ethylene is about 74% and the yield per pass is 70%. The ethylene yield per pass generally reaches a maximum at an ethane conversion of about 90%. This means that in a process using air as the source of oxygen, in which it is not practical to recycle the unreacted ethane because of dilution with nitrogen, it would be desirable to run with a conversion which maximizes the yield per pass. On the other hand, with a process using oxygen gas, in which unreacted ethane can be recycled, it would be preferable to run at a much lower conversion in order to take advantage of the higher ethylene yield. Hence, the operation may be carried out either in a single pass where the oxygen is supplied by air and where a lower yield, offset by a savings in equipment and operational costs, is acceptable; or as a multipass operation where pure oxygen is used and where a high yield is the primary consideration.

The molar ratio of chlorine:ethane ranges preferably between from about 0.4 to 0.6:1 for the recovery of vinyl chloride as product in the overall process. The theoretical chlorine/ethane molar ratio for the production of vinyl chloride in the overall process is 0.5:1. Where vinyl chloride is to be the desired product, chlorine/ethane ratios higher than 0.6 can be used. However, more hydrogen chloride will be produced in the autothermic cracking step than is required for subsequent oxyhydrochlorination of ethylene when the chlorine/ethane ratio is greater than 0.6. To avoid an excess of hydrogen chloride in the overall production of vinyl chloride, it is preferable to keep the molar ratio of chlorine:ethane below about 0.6:1. Ratios below 0.4:1 may be used if desired and high yields may be obtained, but the need for recycling ethane increases as the ratio of chlorine:ethane is lowered.

Where ethylene dichloride is to be recovered as a second product in addition to vinyl chloride, the molar ratio of chlorine:ethane is increased to preferably between about 0.6 to 0.9:1. The upper limit of the chlorine/ethane ratio is a function of the amount of ethylene dichloride, as opposed to vinyl chloride monomer, that is to be recovered. The amount of ethylene dichloride withdrawn as product from the system is preferably substantially equivalent in chlorine content to the chlorine used in excess of 0.5:1 molar ratio of chlorine:ethane.

Where ethylene dichloride is to be recovered as product, the molar ratio of chlorine:ethane should range from about 0.9 to 1.2:1, more preferably at 1.0:1.

It is to be understood that any of these combinations of recovered products can be achieved where the chlorine molar ratio based on ethane ranges from 0.2 to 1.2:1. But low chlorine/ethane ratios require considerable recycling of ethane whereas relatively high chlorine/ethane ratios lead to an unwanted excess of hydrogen chloride. It is a feature of the process of the present invention, that vinyl chloride, vinyl chloride together with ethylene dichloride in any desired proportion, or ethylene dichloride, can be recovered without an excess of unwanted hydrogen chloride as by-product. Where vinyl chloride is the desired product to be recovered, the molar ratio of chlorine:ethane is most desirably about 0.5:1. Where ethylene dichloride is the desired product, the molar ratio of chlorine:ethane is most desirably 1.0:1. Where the desired products are vinyl chloride and ethylene dichloride, the molar ratio of chlorine to ethane is preferably selected with respect to the relative quantities of each product to be recovered, so that no appreciable excess of unwanted hydrogen chloride is produced.

The amount of chlorine which can be reacted in the process of our invention depends on the overall hydrogen chloride (HCl) balance. A half mol of chlorine will form one mol of HCl. A second mol of HCl is formed by the thermal cracking of ethylene dichloride, giving the required two mols of HCl for the oxyhydrochlorination. Hydrogen which cannot be removed from the ethane by reaction with chlorine must be removed by reaction with oxygen. In actuality, somewhat less than the theoretical amount of oxygen can be used, as a certain amount of hydrogen is also removed as molecular hydrogen by thermal dehydrogenation. If the chlorine-to-ethane ratio is increased, the oxygen-to-ethane ratio may be decreased.

The factors involved in maintaining the temperature of the autothermic reaction zone from about 700° C. to below 1000° C., or preferably between about 850° C. to 950° C., include the amount of oxygen introduced with the chlorine, the degree of preheating of the feed gases, the retention time, the possible application of external heat, and the degree of thermal insulation. Although either air or substantially pure oxygen gas can be used in both the autothermic cracking unit and in the oxyhydrochlorinator to follow, the use of substantially pure oxygen will permit the use of smaller preheaters and an appreciable reduction in the size of the scrubbing system required. The use of substantially pure oxygen gas also provides considerable yield improvement, particularly because ethane can be recovered and recycled. The feed rate into the reactor is correlated with reactor dimensions to preferably give a residence time in the autothermic reaction zone of between about 0.25 to 2.5 seconds.

The mol ratio of the oxygen:ethane in the autothermic reaction zone feed is in the range of about 0.005 to 0.5:1, preferably about 0.1 to 0.4:1. The lower ratios improve the ethylene yield by reducing carbon monoxide methane formation, but also decrease the heat of reaction. The use of these lower ratios requires that the reactants be preheated to a higher temperature. The residence time in the reactors themselves is so short that little heat can be transferred there. Hence we depend on the heat of reaction to raise the reactants to the desired reaction temperature. If the oxygen-to-ethane ratio is adjusted downward to give a near zero heat of reaction, then the reactant preheat temperatures are preferably such that the desired reactor temperature is attained before introduction of the reactants into the reactor. In general, this is not very practical, so that the oxygen-to-ethane ratio is preferably kept high enough to give a significant temperature rise due to heat of reaction. This temperature rise is increased by using oxygen rather than air, so that required preheat temperatures are then reduced.

We have obtained high conversions of ethane to ethylene where the reaction zone includes any conventional gas-gas reactor which will not tend to enhance either reactor plugging or substantial product yield loss when ethane, oxygen and chlorine are the reactants therein. An example of such a reactor is disclosed in U.S. patent application Ser. No. 167,733, filed July 30, 1971 by Bruce E. Kurtz and entitled "Isothermal Chlorination of Methane, Ethane and Other Compounds in a Porous Tube Reactor".

The autothermic cracking reaction products are next quenched with a volatile liquid which cools the reaction products and which can be added to the reaction products as they leave the reaction zone, or injected directly into the reaction zone at a point to permit the desired retention time at the desired autothermic reaction temperatures before quenching. Suitable quench liquids include carbon tetrachloride, chlorinated biphenyls or water. Water is preferred because it is especially effective in suppressing carbon formation.

The volatile quenching liquid is introduced into the reaction product gases in an amount to, by vaporization, cool the gases to a temperature below about 600° C., preferably below about 500° C. The point of introduction of the quench is a major factor in establishing the residence time of the reactants in the reaction zone. Good results have been obtained by introducing the quench directly into the reactor at a point opposite that at which the preheated reactants are introduced. Quenching per se has little effect on conversions or yields, but is important in suppressing carbon formation and preventing reactor plugging.

The quenched gases preferably pass next to a scrubber, the design of which is not critical. Its purpose is to remove particulate carbon from the product of the autothermic reactor. It may consist of a spray tower with a small amount of the quenching liquid, preferably water, circulated by a pump to form a spray. The scrubber generally operates at between about 100° C. and 200° C., so that the exit is vapor phase. A solids separator is placed in the line to trap the carbon for removal. A liquid cyclone represents one type of solids separator.

The autothermic reaction zone product gases are preferably reheated by a heat exchanger to at least about 150° C. to 200° C. This exchanger may if desired be included in a "hot box" or cabinet furnace with other heat exchangers. Preferably the gases next pass to a conventional catalytic hydrogenator to convert any acetylene present to ethylene.

2. Oxyhydrochlorination of Ethylene to Produce Ethylene Dichloride

The reaction product gases containing predominantly ethylene and hydrogen chloride are next passed into a catalytically activated oxyhydrochlorination zone together with at least about the stoichiometric amount of oxygen. The oxygen may, if desired, be supplied by air, and may be used in an excess of up to 100 percent or more. The oxyhydrochlorination generally proceeds at a temperature between about 200° C. to 250° C. The hydrogen chloride (HCl) obtained from the autothermic cracking zone is insufficient for this oxyhydrochlorination step if the preferred molar ratio of 0.4 to 0.6:1 of chlorine to ethane has been used, or if the ratio of chlorine to ethane is less than 1.0:1. An additional stream of HCl, however, from the subsequent cracking of ethylene dichloride in an externally heated cracking zone for the production of vinyl chloride may also be directed to the oxyhydrochlorination zone.

Substantially pure ethylene dichloride may be separated and recovered as product. Where it is desired to recover only ethylene dichloride, no subsequent reaction step is required. Although the molar ratio of chlorine:ethane may be taken between 0.2:1 and 1.2:1, it is preferred that the molar ratio of chlorine:ethane be held between 0.9:1 and 1.2:1. The most preferred molar ratio of chlorine/ethane in the production of ethylene dichloride as desired final product is the theoretical molar ratio of 1.0:1 because undue recycling and production of an excess of hydrogen chloride is avoided.

The product of the oxyhydrochlorinator preferably passes to a conventional recovery system having distillation or stripping columns. Water and non-condensibles are separated. The latter may contain ethane, methane, carbon monoxide, and oxygen. If substantially pure oxygen gas rather than air has been used in the process, the ethane obtained at this point, after removal of any carbon monoxide and purging of methane, may be returned as recycle to the autothermic cracking reactor.

3. Cracking of Ethylene Dichloride to Vinyl Chloride Monomer

The ethylene dichloride produced by oxyhydrochlorination may be passed to an externally heated cracking zone comprising a continuously heated tubular furnace maintained at a temperature such that the products exit at about 500° C. to 600° C. On cracking of ethylene dichloride to vinyl chloride, hydrogen chloride and ethylene dichloride are also recovered. The ethylene dichloride which is unreacted is recycled to the entrance to the externally heated cracking zone. The hydrogen chloride is directed to the oxyhydrochlorination zone to supply the amount of hydrogen chloride which is required for the oxyhydrochlorination. The vinyl chloride is recovered as product.

If it is desired to simultaneously produce ethylene dichloride with the vinyl chloride, an excess of chlorine ranging from about 0.6 to 0.9 mol per mol of ethane may be used, with the continuous withdrawal of an amount of ethylene dichloride from the oxyhydrochlorination step sufficient to maintain a balance between the HCl produced and that consumed. No catalyst need be employed and the temperature is maintained by external heating so that the cracked gases containing vinyl chloride exit at between about 500° C. and 600° C. These gases leaving the externally heated cracking zone may enter a recovery system which may consist of a series of distillation or stripping columns.

The hydrogen chloride formed in cracking the ethylene dichloride, as previously explained, may be passed to the oxyhydrochlorinator. If the system is run in proper balance, the hydrogen chloride entering the oxyhydrochlorinator from the autothermic cracking unit and that from the externally heated ethylene dichloride cracking zone, equal that needed in the oxyhydrochlorination of the ethylene. Unreacted ethylene dichloride bottoms from the recovery system are recycled to the ethylene dichloride cracking zone, and the separated vinyl chloride is removed as product.

EXAMPLES 1 – 6

In the case of Examples 1–3, ethane was introduced into the top of the reaction zone at the rate of 12.5 grams per minute (g/m). In Example 4, the rate was 6.2 grams of ethane per minute; in Example 5, 12.5 g/m and in Example 6, 25.0 g/m. The ethane and oxygen were preheated to about 500° C. and the chlorine to about 400° C. before entering the reactor zone.

The progress of the autothermic cracking step and control of the operation was obtained by taking periodic samples for analysis. A thermocouple extended into the reaction zone for temperature determination.

The operating conditions, yields and by-products are given in Table I.

In the above runs air was used rather than substantially pure oxygen gas. Examples 1, 2 and 3 illustrate the favorable effect of increasing the chlorine to ethane feed ratio. In Example 3, about 1.14 mols of HCl were obtained because the chlorine used was in excess of 0.5 mols. Only 1.0 mol of HCl is required for the balanced production of vinyl chloride. Examples 4, 5 and 6 illustrate the minor effect of decreasing residence time.

The average yield of vinyl chloride based on ethane is 90 percent and based on chlorine is 95 percent when using oxygen. When air is used rather than substantially pure oxygen gas in the autothermic cracking step and the oxyhydrochlorination operation, the yield of vinyl chloride drops to about 70 percent. This is primarily because the ethane recovered is diluted with nitrogen and cannot readily be recycled.

EXAMPLE 7

In this run the chlorine and oxygen entered the autothermic reactor from the bottom, and the ethane also entered at the bottom at a rate of 12.5 grams per minute. The reaction gases exited through a side arm at the top of the cylindrical reactor. In this Example, quench liquid was vaporized in the quenching operation, and the reaction gases, together with the vaporized quench liquid, exited the reactor at a temperature of 500° C.

The operating conditions, yields and by-products obtained in Example 7 are also included in Table I for comparison. A lower reaction temperature (850° C.) was used, compensated for by a longer residence time.

EXAMPLE 8

The preheated ethane entered the reactor at a rate of 25 grams per minute. The reactor had a side opening for exit gases and a top-center quench liquid inlet, as with Example 7. The results of this run are also tabulated in Table I for comparison.

As in the case of Example 7, the autothermic reaction, as a result of lower oxygen input, ran at lower temperature compensated for by a longer residence time. The overall yield was slightly below that of Example 7. Here also, somewhat more acetylene and methane were produced.

EXAMPLE 9

Ethane preheated to 500° C. was passed into the reactor at a rate of 12.5 grams per minute. A mixture of preheated oxygen at 600° C. and preheated chlorine at 400° C. was also passed therein simultaneously with the ethane. The molar ratio of the chlorine:ethane was 0.57:1.0 and the molar ratio of oxygen:ethane was 0.22:1.0. The reaction temperature was 950° C. The results of the autothermic cracking reaction are tabulated in Table I.

In the production of vinyl chloride from this reaction mixture, the reaction products, predominantly ethylene

TABLE I

| | | | | EXAMPLES 1 – 9 INCLUSIVE | | | | | | | | |
|---|---|---|---|---|---|---|---|---|---|---|---|---|
| Example | Reactor Temp. °C. | Ethane Feed g/m | Residence Time Seconds | $Cl_2/C_2H_6$ Mol ratio | $O_2/C_2H_4$ Mol ratio | $C_2H_6$ Conv. Percent | $C_2H_4$ Yield % | $C_2H_4$ Yield/pass % | Mols By-Products Per 100 mols $C_2H_4$ | | | |
| | | | | | | | | | $CH_4$ | CO | $CO_2$ | $C_2H_2$ |
| 1 | 900 | 12.5 | 0.29 | 0.19 | 0.09 | 76.6 | 87.2 | 66.8 | 14.0 | 14.8 | 0.3 | 0 |
| 2 | 900 | 12.5 | 0.26 | 0.38 | 0.09 | 85.1 | 87.4 | 74.4 | 12.6 | 15.2 | 0.4 | 0 |
| 3 | 900 | 12.5 | 0.24 | 0.57 | 0.09 | 91.7 | 86.9 | 79.7 | 11.2 | 10.4 | 0.4 | 0 |
| 4 | 900 | 6.2 | 0.43 | 0.38 | 0.19 | 92.7 | 75.7 | 70.2 | 23.6 | 32.1 | 0.9 | 0 |
| 5 | 900 | 12.5 | 0.21 | 0.38 | 0.19 | 93.9 | 80.4 | 75.5 | 17.2 | 27.0 | 0.8 | 0 |
| 6 | 900 | 25.0 | 0.11 | 0.38 | 0.19 | 88.4 | 81.2 | 71.8 | 16.2 | 27.3 | 0.6 | 0 |
| 7 | 850 | 12.5 | 1.12 | 0.50 | 0.08 | 94.5 | 80.9 | 76.4 | 22.8 | 18.2 | 3.3 | 1.5 |
| 8 | 850 | 25.0 | 1.68 | 0.50 | 0.08 | 89.9 | 80.9 | 72.7 | 24.4 | 17.2 | 1.2 | 2.2 |
| 9 | 950 | 12.5 | 0.18 | 0.57 | 0.22 | 89.3 | 87.6 | 78.2 | 39.7 | 11.1 | 1.3 | 2.6 |

(1 mol) and hydrogen chloride (1.14 mols), react in the presence of a slight excess of oxygen and an additional 0.86 mol of hydrogen chloride in a catalytic oxyhydrochlorinator to produce a mol of ethylene dichloride.

Ethylene dichloride amounting to 0.14 mol is withdrawn as a first product, and the remaining 0.86 mol subjected to thermal cracking in a tubular furnace heated to a degree such that the reactants exit at between about 500° C. and 600° C. Unreacted ethylene dichloride is recovered and recycled to the furnace.

When vinyl chloride is recovered as a second product, the 0.86 mol of hydrogen chloride obtained from the vinyl chloride production step, together with the 1.14 mols of hydrogen chloride obtained from the autothermic cracking step, comprise the two mols of HCl required in the oxyhydrochlorination of 1.0 mol of ethylene. Thus, by using an excess of chlorine in the autothermic reactor and bleeding ethylene dichloride from the system in an amount corresponding to the excess of chlorine used, both ethylene dichloride and vinyl chloride can be manufactured without the production of unwanted hydrogen chloride.

Since changes may be made in carrying out the above process without departing from the scope of the invention, it is intended that all matter contained in the above description shall be interpreted as illustrative and not in a limiting sense.

We claim:

1. The process for making vinyl chloride from ethane comprising the steps of:
   a. reacting a gaseous stream containing ethane, chlorine and oxygen in mol ratio of chlorine to ethane of from about 0.4:1 to 0.6:1, and oxygen to ethane in mol ratio of from about 0.1:1 to 0.4:1, under non-catalytic, autothermic conditions at a temperature within the range of from about 700° C to below 100° C for a time period of from about 0.1 to 10 seconds to obtain a gas stream comprising ethylene and hydrogen chloride;
   b. passing said gas stream comprising ethylene and hydrogen chloride together with the hydrogen chloride obtained in step c, below, and with oxygen in at least about stoichiometric amount through a catalytically activated oxyhydrochlorination zone under oxyhydrochlorination condition to convert the ethylene to ethylene dichloride, and recovering the ethylene dichloride; and
   c. thermally cracking the ethylene dichloride to obtain vinyl chloride and hydrogen chloride, recovering the vinyl chloride, and recycling the hydrogen chloride to step (b), above.

2. The process for making ethylene from ethane which comprises reacting a gaseous stream containing ethane, chlorine and oxygen in mol ratio of chlorine to ethane of from about 0.2:1 to 1.2:1, and mol ratio of oxygen to ethane of from about 0.005:1 to 0.5:1, under non-catalytic, autothermic conditions at temperature within the range of from about 700° to below 1000° C. for a time period of from about 0.1 to 10 seconds to obtain a gas stream comprising ethylene, hydrogen chloride and water.

3. The process of claim 2 wherein reaction is conducted at temperature within the range of from about 850° to 950° C. for a time period of from about 0.25 to 10 seconds.

4. The process of claim 2 wherein the mol ratio of chlorine to ethane is from about 0.4:1 to 0.6:1 and the mol ratio of oxygen to ethane is from about 0.1:1 to 0.4:1.

5. The process of claim 4 wherein reaction is conducted at temperature within the range of from about 850° to 950° C. for a time period of from about 0.25 to 10 seconds.

* * * * *